United States Patent
Yang

(10) Patent No.: US 6,852,309 B2
(45) Date of Patent: Feb. 8, 2005

(54) GELATIN SOFT CAPSULE HAVING THE PROPERTIES OF REMOVAL OF ORAL SMELL AND CLEANING OF ORAL CAVITY

(75) Inventor: Joo Hwan Yang, Kyonggi-Do (KR)

(73) Assignee: Suheung Capsule Co., LTD, Kyonggi-do (KR)

( * ) Notice: Subject to any disclaimer, the term of this patent is extended or adjusted under 35 U.S.C. 154(b) by 0 days.

(21) Appl. No.: 10/382,907

(22) Filed: Mar. 7, 2003

(65) Prior Publication Data

US 2004/0013722 A1 Jan. 22, 2004

(30) Foreign Application Priority Data

Jul. 18, 2002 (KR) ................................ 10-2002-0041890

(51) Int. Cl.⁷ ............................ A61K 7/26; A61K 7/00; A61K 7/16; A61K 9/00; A61K 9/48
(52) U.S. Cl. ........................... 424/58; 424/49; 424/400; 424/451; 424/456
(58) Field of Search ................................ 424/400, 451, 424/456, 49, 58

(56) References Cited

U.S. PATENT DOCUMENTS

| 4,935,243 A | * | 6/1990 | Borkan et al. ............... 424/441 |
| 2003/0017209 A1 | * | 1/2003 | Parikh et al. ................ 424/492 |
| 2003/0138483 A1 | * | 7/2003 | Petriconi et al. ............ 424/456 |

* cited by examiner

*Primary Examiner*—Thurman K. Page
*Assistant Examiner*—Simon J. Oh
(74) *Attorney, Agent, or Firm*—Jacobson Holman PLLC

(57) ABSTRACT

The present invention relates to a gelatin soft capsule having the properties of removal of oral smell and cleaning of oral cavity, which contains the ingredient for masking an oral smell as an active ingredient. More particularly it relates a gelatin soft capsule comprising core ingredients and shell ingredients, wherein said core ingredients comprise i) 40~90 wt % of at least one base material selected from safflower seed oil, olive oil and medium chain triglycerides, ii) 1~40 wt % of natural or artificial flavor for refreshing oral cavity, iii) 0.1~10 wt % of at least one artificial sweetener selected from saccharine, aspartam and stevioside; and said shell ingredients comprise the gelatin as a base material, glycerin, D-sorbitol, citric acid, surfactant and edible pigment.

2 Claims, No Drawings

GELATIN SOFT CAPSULE HAVING THE PROPERTIES OF REMOVAL OF ORAL SMELL AND CLEANING OF ORAL CAVITY

BACKGROUND OF THE INVENTION

The present invention relates to a gelatin soft capsule having the properties of removal of oral smell and cleaning of oral cavity, which contains the ingredient for masking an oral smell as an active ingredient. More particularly, the present invention relates to a soft capsule having the properties of removal of oral smell and cleaning of oral cavity, which is prepared by modifying the double layer stream method comprising i) dropping the core solution and shell solution by free dropping or pulsating supply pump, ii) cutting them by the cooling solution pulse, iii) encapsulating the core solution with shell solution in a seamless manner.

The seamless gelatin soft capsule of the present invention is manufactured by following ingredients, which are, the ingredients of core solution of soft capsule comprising i) one or more selected from safflower seed oil, olive oil, medium chain triglycerides as a base material, ii) one or more natural or artificial flavor for refreshing oral cavity selected from menthol, peppermint flavor, spearmint flavor, parsley flavor, iii) artificial sweetener, as well as the ingredients of shell solution comprising the gelatin as a base material, glycerin, D-sorbitol, citric acid, surfactant and edible pigment. Further, the soft capsule of the present invention has the merits of convenience of portable storage and use.

For refreshing and cleaning the oral cavity, many kinds of liquid type oral cleansers have been commercially marketed. For example, Care Gargle™ containing benzetonium chloride, Gargreen Mint™ containing CPC and xylitol, Pro Fresh containing polyphenols and aloe, Gargreen Tent™ containing xylitol, Retradex™ containing aloe vera, chlorophyll and mint flavor and oral cleanser containing cinnamon extract have been developed and marketed. As the packings of such liquid type oral cleanser, bottle packing or pouch pack has been developed.

On the other hand, some candies for removing oral smell and chewing gums containing various flavors or oral cleaning agent, such as, cethyl pyridium chloride have been also developed and commercially marketed.

However, such liquid type of oral cleanser has some drawbacks, because it has large volume and weight. Further, it requires additional cup and bottle for using it, which causes the inconvenience of use. Of course, the gargling the liquid oral cleanser and throwing it out from oral cavity are very inconvenient for user.

To meet above requirements, the inventor of the present invention has developed a gelatin soft capsule having the properties of removal of oral smell and cleaning of oral cavity. Further, the gelatin soft capsule of the present invention has many merits; i) convenient use of soft capsule by chewing it in the oral cavity in a small amount, ii) portable storage for one or daily amount, iii) no need of additional device for use, for example, cup or bottle.

SUMMARY OF THE INVENTION

The object of the present invention is to provide a gelatin soft capsule having the properties of removal of oral smell and cleaning of oral cavity comprising core ingredients and shell ingredients, wherein said core ingredients comprise i) 40~90 wt % of at least one base material selected from safflower seed oil, olive oil and medium chain triglycerides, ii) 1~40 wt % of natural or artificial flavor for refreshing oral cavity, iii) 0.1~10 wt % of at least one artificial sweetener selected from saccharine, aspartam and stevioside; and said shell ingredients comprise the gelatin as a base material, glycerin, D-sorbitol, citric acid, surfactant and edible pigment.

Said safflower seed oil contains 72~82 wt % of linoleic acid, and said olive oil contains 65~80 wt % of oleic acid.

Further, said natural or artificial flavor is at least one selected from the group consisting of orange flavor, strawberry flavor, grape flavor, peppermint flavor, spearmint flavor, menthol, anenol, oegenol, wintergreen flavor, mint flavor, sage, eucalyptus oil, fruit extract and rosemary.

Further, the composition of shell ingredients is i) 10~50 wt % of gelatin, ii) 10~30 wt % of glycerin, iii) 1~20 wt % of D-sorbitol solution, iv) 0.1~5 wt % of surfactant selected from sodium lauryl sulfate, sucrose fatty acid ester, diacetylene monoglyceride, glacial acetic acid and sorbitan fatty acid ester, v) proper amount of purified water and vi) small amount of citric acid and edible pigment.

DETAILED DESCRIPTION OF THE INVENTION

The oral smell is generally believed to be caused by a mixture of odor generated an oral cavity from ingested food and odor returned to the oral cavity from the stomach after digesting food. The elimination of oral smell is very important for personal hygiene and face-to-face relationship.

The present invention has developed a seamless gelatin soft capsule for removal of oral smell and cleaning of oral cavity modified by double layer stream method. For using a soft capsule of the present invention, 1 or 2 soft capsule is inserted and chewed in the oral cavity. Then, the natural oil and the flavor in the soft capsule refresh the oral cavity after they are dissolved in the oral cavity.

The soft capsule of the present invention is manufactured by dropping the core and the shell solution in the double layer stream to maintain the taste and flavor of ingredients for a long time.

As a base material, safflower seed oil containing high level of linoleic and is preferable. As a natural or artificial flavor, wintergreen-aromatic ester salicylate, spearmint-cyclic terpene alcohol or L-menthol is preferable. Further, as a sweetener, saccharine, aspartam or stevioside is preferable. To make a core of soft capsule, base material, natural or artificial flavor, sweetener is mixed and homogenized having the particle size less than 100 micron. Then mixture is filtered and cooled at the room temperature.

To make a shell of soft capsule, the shell solution is prepared in a conventional method with gelatin, glycerin and D-sorbitol solution as plasticizer, and purified water. Then, citric acid as stabilizer and surfactant are added to maintain the physical properties of shell.

The composition of shell contains 10~50 wt % of gelatin, 10~30 wt % of glycerin, 1~20 wt % of D-sorbitol solution, 0.1~5 wt % of surfactant selected from sodium lauryl sulfate, sucrose fatty acid ester, diacetylene monoglyceride, glacial acetic acid and sorbitan fatty acid ester, proper amount of purified water and small amount of citric acid and edible pigment.

The soft capsule of the present invention is manufactured by the soft capsule machine with core solution and shell solution in a seamless method. The weight of soft capsule is 50~300 mg/capsule.

The present invention can be explained more concretely by following examples, but the scope of the present invention shall not be limited by following examples.

EXAMPLE 1

Preparation of Soft Capsule

In this example, the weight of soft capsule is designed as 50 mg. The core solution comprising 70~80 wt % of safflower seed oil; 15~17 wt % of peppermint flavor; 2~5 wt % of wintergreen; 1~3 wt % of aspartam; and 1~2 wt % of parsley seed oil are mixed and homogenized. Then, the particle size of core ingredients are made to be less than 100 micron. On the other hand, the shell solution comprising 30~50 wt % of gelatin (220~250 bloom); 10~20 wt % of glycerin and D-sorbitol solution; 0.1~1 wt % of surfactant selected from the sodium lauryl sulfate, sucrose fatty acid ester, diacetylene monoglyceride, glacial acetic acid and sorbitan fatty acid ester proper amount of purified water; and small amount of citric acid and edible pigment are mixed and aged. Finally, soft capsule is manufactured with core solution and shell solution in a seamless manner.

EXAMPLE 2

The soft capsule is prepared as the same manner in example 1 except that the weight of soft capsule is 200 mg.

EXAMPLE 3

In this example, the weight of soft capsule is designed as 50 mg. The core solution comprising 60~70 wt % of safflower seed oil; 15~20 wt % of spearmint flavor; 2~5 wt % of wintergreen; 1~3 wt % of aspartam; and 1~2 wt % of parsley seed oil are mixed and homogenized. Then, the particle size of core ingredients are made to be less than 100 micron. On the other hand, the shell solution comprising 30~50 wt % of gelatin (220~250 bloom); 10~20 wt % of glycerin and D-sorbitol solution; 0.1~1 wt % of surfactant selected from the sodium lauryl sulfate, sucrose fatty acid ester, diacetylene monoglyceride, glacial acetic acid and sorbitan fatty acid ester proper amount of purified water; and small amount of citric acid and edible pigment are mixed and aged. Finally, soft capsule is manufactured with core solution and shell solution in a seamless manner.

EXAMPLE 4

The soft capsule is prepared as the same manner in example 3 except that the weight of soft capsule is 200 mg.

EXAMPLE 5

Functional Test

The functional test between gelatin soft capsules prepared by above examples 1~4 and a commercially marketed liquid type oral cleanser has been carried out. Followings are protocol and results.

1) Selection of Panel

Total 10 well-trained panels with 5 men and 5 women (age: 20~40) are selected.

2) Method

To compare the function of removal of oral smell between soft capsules and commercially marketed liquid type oral cleanser, the tests are carried out in 3 cases; i) against oral smell occurred from ingested food before having a lunch; ii) against oral smell occurred after having a lunch; and iii) against oral smell occurred smoking a cigaret by lapse of 10 minutes. Soft capsules prepared in the examples and a commercially marketed liquid type oral cleanser are used for functional test. The soft capsules are inserted and chewed in a oral cavity and 20 ml of the liquid type oral cleanser is gargled and threw off. The test has been carried out for 5 days by repeating the test in the same manners.

3) Result

The test points are i) the degree of removal of oral smell, ii) taste and flavor and iii) convenience. The result is indicated by the numbers, on condition that the average point is 5, the worst point is 1 and the best point is 10.

(Score: the worst←1 2 3 4 5 6 7 8 9 10→the best)

The Table 1 shows the result of functional test from man panels.

TABLE 1

| | Example 1, 2, 3, 4 | | | | Liquid type oral cleanser | | | |
|---|---|---|---|---|---|---|---|---|
| panel | removal of oral smell | taste and flavor | convenience | total | removal of oral smell | taste and flavor | convenience | total |
| 1 | 8 | 9 | 9 | 9 | 5 | 6 | 5 | 5 |
| 2 | 7 | 9 | 9 | 9 | 6 | 7 | 5 | 5 |
| 3 | 8 | 8 | 9 | 9 | 7 | 6 | 6 | 6 |
| 4 | 9 | 9 | 9 | 8 | 6 | 7 | 6 | 5 |
| 5 | 8 | 9 | 7 | 9 | 6 | 6 | 6 | 5 |
| total | 40 | 44 | 43 | 44 | 30 | 32 | 28 | 26 |

The Table 2 shows the result of functional test from woman panels.

TABLE 2

| | Example 1, 2, 3, 4 | | | | Liquid type oral cleanser | | | |
|---|---|---|---|---|---|---|---|---|
| panel | removal of oral smell | taste and flavor | convenience | total | removal of oral smell | taste and flavor | convenience | total |
| 1 | 8 | 9 | 9 | 9 | 5 | 6 | 5 | 5 |
| 2 | 7 | 9 | 9 | 9 | 6 | 7 | 5 | 5 |
| 3 | 8 | 8 | 9 | 9 | 7 | 6 | 6 | 6 |
| 4 | 9 | 9 | 9 | 8 | 6 | 7 | 6 | 5 |
| 5 | 8 | 9 | 7 | 9 | 6 | 6 | 6 | 5 |
| total | 40 | 44 | 43 | 44 | 30 | 32 | 28 | 26 |

The soft capsules of example 1~4 show the better property of removal of oral smell compared to commercially marketed liquid type oral cleanser.

Therefore, the soft capsules of the present invention has many merits compared to conventional liquid type of oral cleanser in many fields, for example, i) better taste and flavor, ii) convenient use by chewing it in the oral cavity in a small amount, iii) portable storage for one or daily amount, iv) no need of additional device for use, for example, cup or bottle.

Further, the soft capsule of the present invention makes effective masking of oral smell occurred from the ingested food before having a lunch, after having a lunch, and from smoking a cigaret.

What is claimed is:

1. A gelatin soft capsule having the properties of removal of oral smell and cleaning of oral cavity comprising core ingredients and shell ingredients, wherein said core ingredients comprise
   i) 40–90 wt % of at least one base material selected from safflower seed oil, olive oil and medium chain triglycerides,
   ii) 1–40 wt % of natural or artificial flavour for refreshing oral cavity,
   iii) 0.1–10 wt % of at least one artificial sweetener selected from saccharine, aspartam and stevioside; and said shell ingredients comprise i) 10–50 wt % of gelatin, ii) 10–30 wt % of glycerin, iii) 1–20 wt % of D-sorbitol solution, iv) 0.1–5 wt % of surfactant selected from the group consisting of sodium lauryl sulfate sucrose fatty acid ester, diacetylene monoglyceride, glacial acetic acid or sorbitan fatty acid ester, v) proper amount of purified water, and small amount of citric acid and edible pigment.

2. The gelatin soft capsule having the properties of removal of oral smell and cleaning of oral cavity according to claim 1, wherein said safflower seed oil contains 72–82 wt % of linoleic acid, and said olive oil contains 65–80 wt % of oleic acid.

* * * * *